United States Patent [19]

Crews et al.

[11] Patent Number: 5,377,618

[45] Date of Patent: Jan. 3, 1995

[54] METHOD FOR PREFERENTIAL PRODUCTION OF RATITES OF A DESIRED SEX

[75] Inventors: David Crews; Thane Wibbels, both of Austin, Tex.

[73] Assignee: Reproductive Sciences, Inc., Austin, Tex.

[21] Appl. No.: 922,831

[22] Filed: Jul. 31, 1992

[51] Int. Cl.$^6$ ............... A01K 67/04; A61K 31/56
[52] U.S. Cl. ................................ 514/182; 119/6.8
[58] Field of Search ..................... 119/6.8; 514/182

[56] References Cited

U.S. PATENT DOCUMENTS

| | | | |
|---|---|---|---|
| 2,734,482 | 2/1956 | Seltzer | 119/6.8 |
| 5,158,038 | 10/1992 | Sheeks et al. | 119/6.8 |
| 5,201,280 | 4/1993 | Crews et al. | 119/174 |

Primary Examiner—Marianne M. Cintins
Assistant Examiner—Kimberly R. Jordan
Attorney, Agent, or Firm—Ansel M. Schwartz

[57] ABSTRACT

The present invention is a method for sex determination in ratites, such as ostriches. The method includes the steps of administering a material that causes sex to be determined to a fertilized ratite egg and incubating the egg until it hatches. Preferably, the administering step includes the step of injecting the material into the egg and preferably before the injecting step, there is the step of drilling a hole into the eggshell of the egg. The material that determines sex in ratites includes natural estrogens or a functionally equivalent amount of its synthetic mimics to cause female development and natural nonaromatizable androgens or a functionally equivalent amount of its synthetic mimics to cause male development. Preferably, the material is estradiol-17beta (for female development) or dihydrotestosterone (for male development). A solution may, for example, be comprised of 1.2 milligrams of estradiol-17beta preferably dissolved in 40 microliters of 95% ethanol, or 7.5 milligrams of dihydrotestosterone preferably dissolved in 100 microliters of 95% ethanol, respectively.

20 Claims, 2 Drawing Sheets

METHOD FOR PREFERENTIAL PRODUCTION OF RATITES OF A DESIRED SEX

FIELD OF THE INVENTION

The present invention is related to hormone-induced sex determination of animals. More specifically, the present invention relates to the control of sex determination and sexual differentiation of ratite birds (e.g. ostrich, emu, rhea, kiwi, and cassowary) by the administration of specific sex determining substances to the egg before sexual differentiation of the embryonic gonads.

BACKGROUND OF THE INVENTION

Repeated efforts to manipulate the primary sex ratio from unity traditionally have been unsuccessful (FIG. 1A). This includes not only breeding for biased sex ratios (e.g., Beamer and Whitten, 1991), but also by hormone manipulation of the embryo (van Tienhoven, 1957; Pincus and Hopkins, 1958). Unless there is differential survivorship, the one-to-one sex ratio will persist throughout life. There is an alternative sex determining mechanism in the higher or amniote (the reptiles, birds and mammals) vertebrates, one that is sensitive to the physical and physiological environment (FIG. 1B). In environmental sex determination, variation in the environment influences profoundly the primary sex ratio.

The fundamental difference between the mechanisms underlying genotypic sex determination (GSD) and environmental sex determination lies in the trigger that initiates sex determination; in the former, gonadal sex is determined at fertilization by the pairing of sex chromosomes, whereas in the latter, gonadal sex is determined much later in embryogenesis as a consequence of the embryo's environment. They are alike, however, in that in both (i) the primary sex determiner operates as a trigger that initiates the cascade of events that shape sex differences, and (ii) hormones secreted by the embryonic gonad govern the subsequent differentiation and development of other components of sexuality (Crews and Bull, 1987; Wilson et al., 1981).

A major variant of environmental sex determination is temperature-dependent sex determination (TSD). TSD was originally discovered in the African rainbow lizard (*Agama agama*) in 1966 by Madeline Charnier. Extensive research has revealed that in many oviparous reptiles, the temperature during the middle-third of embryogenesis is the critical cue determining the gonadal sex of the hatchling (Bull, 1980; Janzen and Paukstis, 1991). In TSD, sex determination operates as a switch mechanism that appears to be absolute; no individuals of ambiguous or intermediate sex are produced (Bull, 1985a and b, 1987a and b; Wibbels et al., 1991a). Because gonadal sex is determined after fertilization and egg-Laying in TSD, the primary sex ratio can be manipulated simply by varying incubation conditions.

Administration of exogenous estrogen to eggs of reptiles with TSD will override the effects of a male-producing temperature, resulting in a female hatchling (reviewed by Raynaud and Pieau, 1985; see also Bull et al., 1988; Crews et al., 1989, 1991; Gutzke and Bull, 1986). Studies at the University of Texas at Austin as well as other institutions have shown that the estrogen acts within a particular time window that corresponds with the window of temperature-sensitivity (Gutzke and Chyimi, 1988; Wibbels et al., 1991b). Further, estrogen treatments mimic the effects of female-producing temperature, resulting in the production of all normal-appearing female hatchlings (Crews et al., 1991). Studies with the leopard gecko lizard (*Eublepharis macularius*), a species with TSD indicate that these estrogen-reversed individuals are functionally female as adults (D. Crews, unpublished data).

Recently, it has been found that if eggs of red-eared sliders (*Trachemys scripta*) are incubated at a temperature that normally results in a 50:50 sex ratio, administration of dihydrotestosterone, a natural nonaromatizable androgen, causes male development (Wibbels et al., 1992). That the androgen must be nonaromatizable is important as administration of testosterone, a natural androgen that is converted by the enzyme aromatase to estradiol, causes female development (Bull et al., 1988; Crews et al., 1989; Gutzke and Bull, 1986).

The prior art shows that like temperature, steroid hormones can guarantee sexual development in TSD reptiles. Further, studies show clearly that male and female development in such species are two interlocking cascades that, depending on the steroid hormone used, can be independently activated.

The method of hormone treating eggs with exogenous sex steroid hormones by dipping or by injection has a long history. It is widely assumed that in species with sex chromosomes that steroid hormones play no role in sex determination and application of exogenous steroid hormones do not alter the primary sex ratio. This is the case in mammals (George and Wilson, 1988). In poultry (e.g., chickens, turkeys, etc.), which also have sex chromosomes, estrogen applied to the embryo will feminize the urogenital system of genetic male hatchlings, but they will revert to male plumage and gonads on attaining puberty; this includes the so-called "Selzer" method (van Tienhoven, 1957; Pincus and Hopkins, 1958). Administration of an aromatase inhibitor causes genetic female chickens to develop as phenotypic males (Elbrecht and Smith, 1992); whether these individuals can reproduce as males remains to be demonstrated.

In modern evolutionary biology, the birds are considered "reptiles" in that they evolved from reptile-like ancestors (see FIG. 2). Ratite birds (e.g. ostrich, emu, rhea, kiwi, and cassowary) represent the most primitive of extant birds. On the basis of skull morphology they are more similar to crocodilians than they are to other birds. Further, despite efforts using karyotyping and molecular genetic techniques for detecting sequence repeats, there is no evidence in the prior art to indicate that the ratites possess distinct sex chromosome as do other "higher" birds. The present invention illustrates that sex determination in the ratite birds, such as ostriches, is similar to that of reptiles with TSD in that sex can be manipulated via treatments of exogenous steroid hormones or their agonists.

SUMMARY OF THE INVENTION

The present invention is a method for sex determination in ratites, such as ostriches. The method includes the steps of administering a material that causes sex to be determined to a fertilized ratite egg and incubating the egg until it hatches. The administering step can be carried out in any convenient manner such that the material penetrates into the egg but does not cause infection. Preferably, the administering step includes the step of injecting the material into the egg and preferably before the injecting step, there is the step of drilling a hole into the eggshell of the egg such as into the air sac of the egg.

The material that determines sex in ratites includes natural estrogens or its synthetic mimics to cause female development and natural nonaromatizable androgens or its synthetic mimics to cause male development. Preferably, the material is estradiol-17beta (for female development) or dihydrotestosterone (for male development). A solution may, for example, be comprised of 1.2 milligrams of estradiol-17beta preferably dissolved in 40 microliters of 95% ethanol, or 7.5 milligrams of dihydrotestosterone preferably dissolved in 100 microliters of 95% ethanol, respectively.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1A:
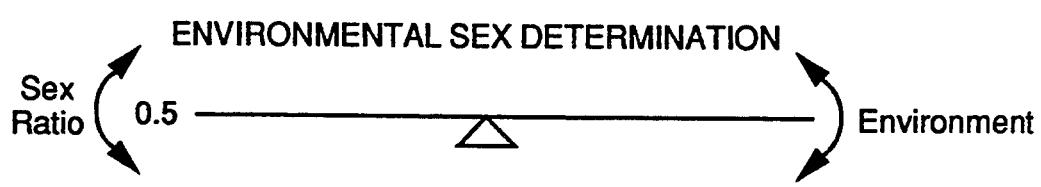
FIGS. 1a and 1b diagrammatically represent the differences in environmental sex determination v. genotypic sex determination.
Figure 1B:
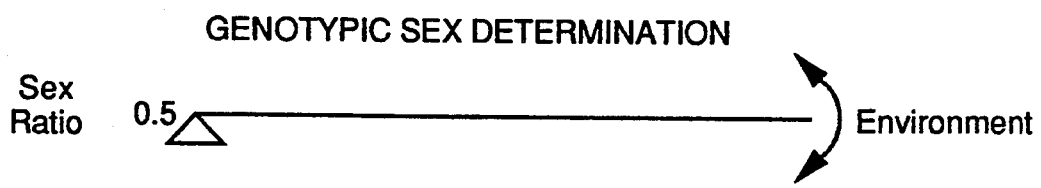
Figure 2:
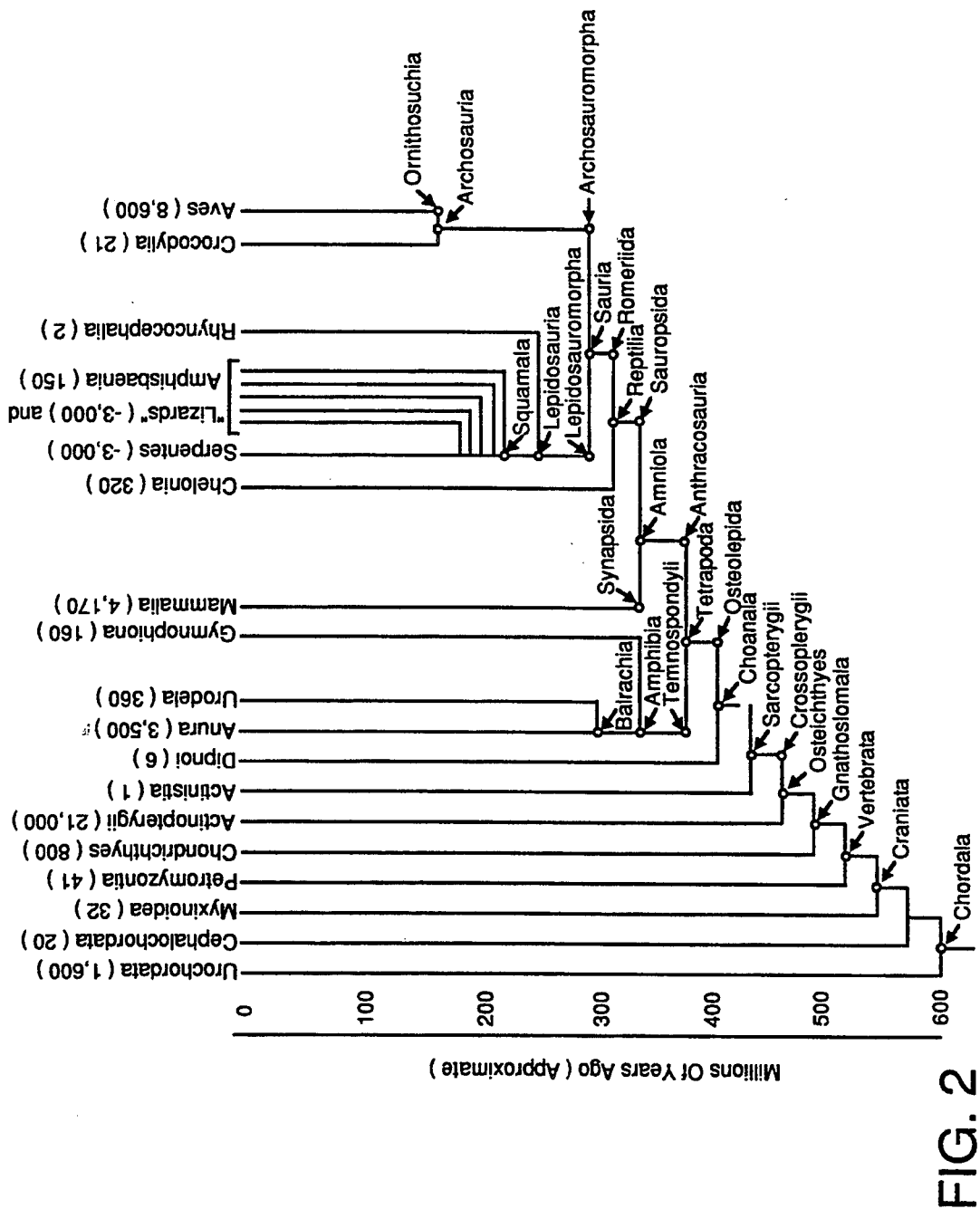
FIG. 2 shows the phylogeny and classification of chordates.

The present invention pertains to a method of sex determination in ratite birds, such as ostriches. Birds are decended from archosaurs and the ratite birds are considered the most primitive group of living birds. As such, they are unlike all other birds in a number of ways. Ratites are not considered poultry, but exotic animals. The two features pertinent to this invention is that (i) ratites appear to lack sex chromosomes, and (ii) administration of exogenous sex hormones determines sex in ratites.

The present invention is a method for sex determination in ratites, such as ostriches. The method includes the steps of administering a material that causes sex to be determined to a fertilized ratite egg and incubating the egg until it hatches. The administering step can be carried out in any convenient manner such that the material penetrates into the egg but does not cause infection. For instance, a pneumatic injector could also be used to introduce the material. Preferably, the administering step includes the step of injecting the material into the egg and preferably before the injecting step, there is the step of drilling a hole into the eggshell of the egg. Preferably, the hole is drilled into the egg above the air sac of the egg.

The material that determines sex in ratites includes natural estrogens or its synthetic mimics to cause female development and natural nonaromatizable androgens or its synthetic mimics to cause male development. Preferably, the material is estradiol-17beta (for female development) or dihydrotestosterone (for male development). A solution may, for example, be comprised of 1.2 milligrams of estradiol-17beta preferably dissolved in 40 microliters of 95% ethanol, or 7.5 milligrams of dihydrotestosterone preferably dissolved in 100 microliters of 95% ethanol, respectively, though the invention is not limited thereto.

Dihydrotestosterone is a natural nonaromatizable androgen that causes male development (Wibbels et al., 1992). That the androgen must be nonaromatizable is important as administration of testosterone, a natural androgen that is converted by the enzyme aromatase to estradiol, causes female development (Bull et al., 1988; Crews et al., 1989; Gutzke and Bull, 1986).

Preferably, before the injection step, there is the step of sterilizing the eggshell surface. This can include the step of painting the location for injection with an antibacterial and antifungal agent. Preferably, the step of injecting occurs after the egg that has been painted with an antibacterial and antifungal agent. The sterilization step kills microorganisms on the eggshell that could infect the egg if they were transported into the egg during the injection process, for example.

The administering step should occur at least before the first ten days of incubation has passed. Preferably immediately after the injecting step, there is the step of sealing any holes in the egg such as with sterile plastic surgery tape. The tape prevents pathogens from entering into the hole of the eggshell. At that point, the egg is then incubated until hatching occurs. The time frame for these steps should be short enough that there is little or no chance of the fertilized egg sustaining damage in any way. Thus, if hormone sex determined individuals are mated with normal animals, viable offspring result.

Example

Eggs of the ostrich (*Struthio camelus*) were injected two to ten days after laying. In each instance, the egg was positioned in a holder attached to a Dremel drill press. The top surface of the egg was cleaned initially with 70% ethanol and then with betadine surgical scrub solution. A Dremel with 0.5 mm in diameter drill bit was used to drill a hole through the apex of the shell. The drill bit was sterilized with 70% ethanol prior to use. A Hamilton 250 microliter syringe was used to inject 1.2 milligrams of estradiol-17beta dissolved in 40 microliters of 95% ethanol into the egg. Injections were performed using a 0.5 inch 30 gauge needle attached to a Hamilton microliter syringe. The hole was then covered with sterile plastic surgery tape and the egg is placed back into the incubator for the remainder of incubation at a temperature of 36.0°±0.1° C. Twenty-three of 24 eggs receiving estradiol-17beta were vent-sexed on hatching as female; while 34 eggs from a non-injected control group from a similar time period produced the normal 50:50 sex ratio. Thus, the method of the present invention successfully determines the sex of ratite eggs.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for preferential production of ratites of a desired sex by treating developing embryos in ova, comprising the steps of:

injecting an effective amount of sex differentiating material into a ratite egg so as to effect development of gonads of the desired sex; and incubating the egg until hatch and thereby obtain a viable ratite of the desired sex.

2. A method as described in claim 1 wherein the egg has an eggshell and before the injecting step, there is the step of sterilizing the eggshell of the egg.

3. A method as described in claim 2 wherein before the injecting step, there is the step of drilling a hole into the eggshell.

4. A method as described in claim 3 wherein after the injecting step, there is the step of sealing the hole.

5. A method as described in claim 4 wherein the sealing step includes the step of sealing the hole with a sterile adhesive tape.

6. A method as described in claim 4 wherein the hole is drilled into the eggshell above the air sac.

7. A method as described in claim 1 wherein the injecting step occurs before the first ten days of incubation have passed.

8. A method as described in claim 7 wherein before the injecting step, there is the step of preparing a bolus of 95% ethanol and estrogen or a functionally equivalent amount of its synthetic mimics to cause female development.

9. A method as described in claim 8 wherein the bolus contains 1.2 milligrams of natural estrogens or a functionally equivalent amount of its synthetic mimics.

10. A method for preferential production of ostriches of a desired sex by treating developing embryos in ova, comprising the steps of:
   injecting an effective amount of sex differentiating material into an ostrich egg so as to effect development of gonads of the desired sex; and
   incubating the egg until hatch and thereby obtain a viable ostrich of the desired sex.

11. A method as described in claim 10 wherein the egg has an eggshell and before the injecting step, there is the step of sterilizing the eggshell.

12. A method as described in claim 11 wherein before the injecting step, there is the step of drilling a hole into the egg.

13. A method as described in claim 12 wherein before the injecting step, there is the step of preparing a bolus of 95% ethanol and estrogen or a functionally equivalent amount of its synthetic mimics to cause female development.

14. A method as described in claim 13 wherein the bolus contains 1.2 milligrams of natural estrogens or a functionally equivalent amount of its synthetic mimics.

15. A method for preferential production of female ratites by treating developing embryos in ova, comprising the steps of:
   placing a tip of a needle through the surface of the ratite egg shell;
   injecting an effective amount of estrogen through the needle into the egg so as to effect development of female gonads; and
   incubating the eggs until hatch and thereby obtain only viable female ratites.

16. A method as described in claim 15 wherein before the placing step, there is the step of drilling a hole into the egg shell.

17. A method for preferential production of female ratites by treating developing embryos in ova, comprising the steps of:
   forcibly injecting estrogen into the egg so as to effect development of female gonads; and
   incubating the eggs until hatch and thereby obtain only viable female ratites.

18. A method as described in claim 17 wherein before the injecting step, there is the step of drilling a hole into the egg shell; and wherein the injecting step includes the step of placing the tip of the needle into the hole.

19. A method for preferential production of female ostriches by treating developing embryos in ova, comprising the steps of:
   placing a tip of a needle through the surface of the ostrich egg shell;
   injecting an effective amount of estrogen through the needle into the egg so as to effect developing of female gonads; and
   incubating the eggs until hatch and thereby obtain only viable female ostriches.

20. A method as described in claim 19 wherein before the placing step, there is the step of drilling a hole into the egg shell; and wherein the placing step includes the step of placing the tip of the needle into the hole.

* * * * *